United States Patent
Coslovi et al.

[11] Patent Number: 6,018,852
[45] Date of Patent: Feb. 1, 2000

[54] TOUCH FASTENER TAPE

[75] Inventors: Giuliano Coslovi, Monza; Piero Rusconi Clerici, Milan, both of Italy

[73] Assignee: Velcro Industries B.V., Curacao, Netherlands Antilles

[21] Appl. No.: 09/032,983

[22] Filed: Mar. 2, 1998

[51] Int. Cl.[7] .................................................. A44B 18/00
[52] U.S. Cl. .................................. 24/442; 24/304; 24/306
[58] Field of Search ............................. 24/442, 306, 304; 156/164

[56] References Cited

U.S. PATENT DOCUMENTS

| | | |
|---|---|---|
| 2,717,437 | 9/1955 | De Mestral . |
| 3,136,026 | 6/1964 | De Mestral . |
| 3,138,841 | 6/1964 | Naimer . |
| 3,279,008 | 10/1966 | Wallach .................................. 24/306 |
| 3,319,307 | 5/1967 | Marforio . |
| 3,387,345 | 6/1968 | Savoir . |
| 3,426,363 | 2/1969 | Girard . |
| 3,594,873 | 7/1971 | Hockmeyer . |
| 3,943,981 | 3/1976 | De Brabander . |
| 3,949,128 | 4/1976 | Ostermeier . |
| 4,290,832 | 9/1981 | Kalleberg . |
| 4,464,217 | 8/1984 | Dickover et al. ..................... 156/164 |
| 4,646,397 | 3/1987 | Yoshida . |
| 4,654,246 | 3/1987 | Provost et al. . |
| 4,665,909 | 5/1987 | Trainor . |
| 4,714,096 | 12/1987 | Guay . |
| 4,878,274 | 11/1989 | Patricy ................................... 24/306 |
| 4,894,060 | 1/1990 | Nestegard ............................. 24/442 |
| 5,081,748 | 1/1992 | Eberle . |
| 5,086,543 | 2/1992 | Mitchell ................................ 24/442 |
| 5,136,759 | 8/1992 | Armour, II . |
| 5,214,874 | 6/1993 | Faulkner ................................ 24/442 |
| 5,369,853 | 12/1994 | Okawa et al. . |
| 5,399,418 | 3/1995 | Hartmanns et al. . |
| 5,436,051 | 7/1995 | Donaruma et al. . |
| 5,457,855 | 10/1995 | Kenney et al. . |
| 5,515,583 | 5/1996 | Higashinaka . |
| 5,659,930 | 8/1997 | Okawa . |
| 5,669,120 | 9/1997 | Wessels et al. . |
| 5,693,401 | 12/1997 | Sommers et al. ..................... 24/442 |

FOREIGN PATENT DOCUMENTS

| | | |
|---|---|---|
| 0604869 | 7/1994 | European Pat. Off. ............... 24/442 |
| 972648 | 10/1964 | United Kingdom . |

*Primary Examiner*—Victor N. Sakran
*Attorney, Agent, or Firm*—Fish & Richardson P.C.

[57] ABSTRACT

The invention features a textile fastener tape characterized by having, in the weft direction across the tape, one or more sections which exhibit elasticity and one or more sections which do not exhibit elasticity. The fastener tape can be a woven or a knitted fabric.

9 Claims, 4 Drawing Sheets

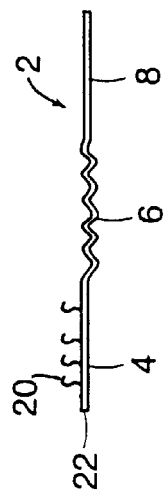
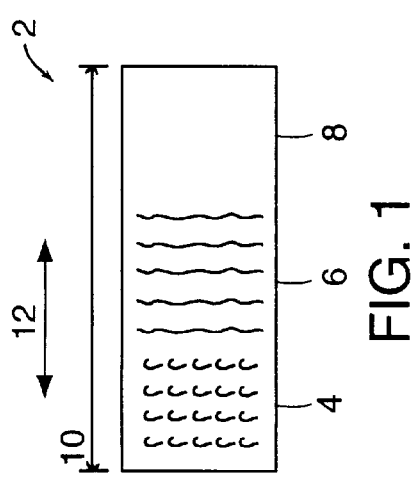
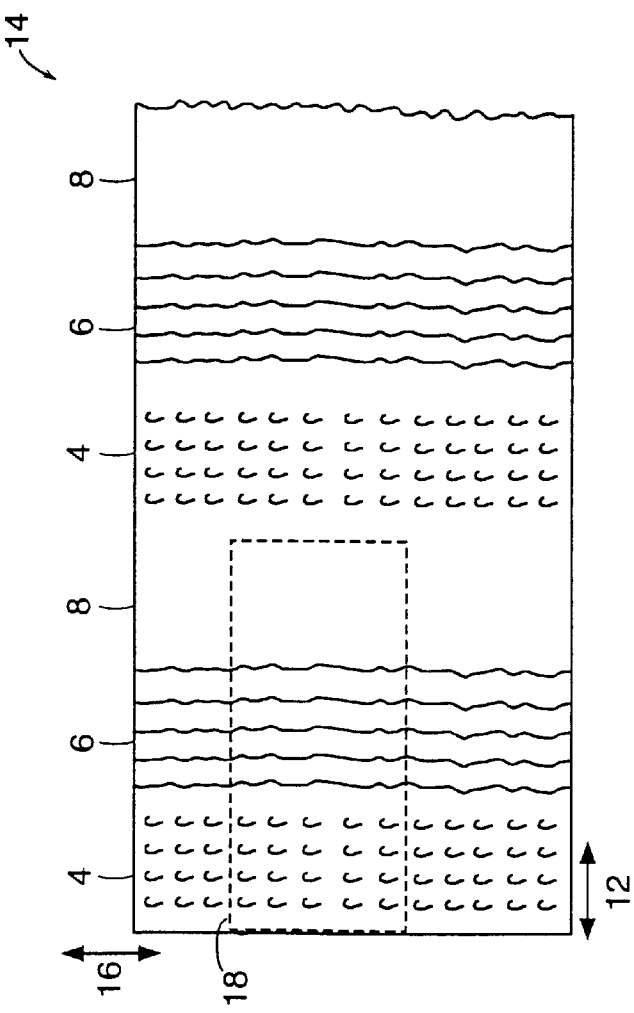

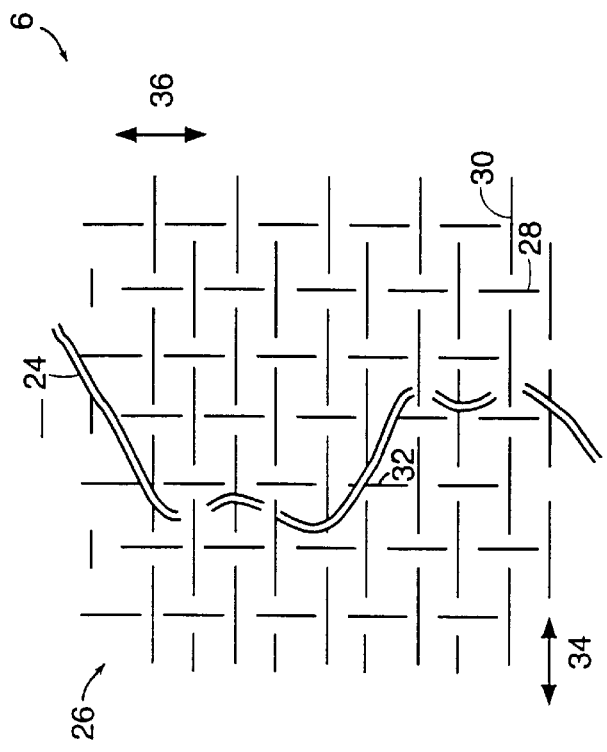
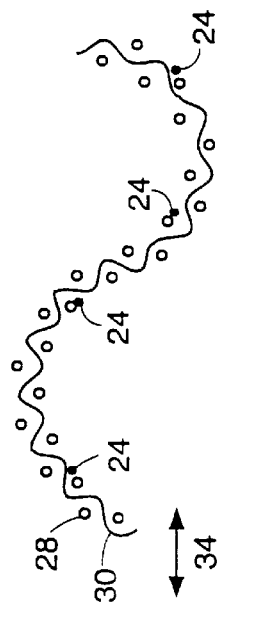
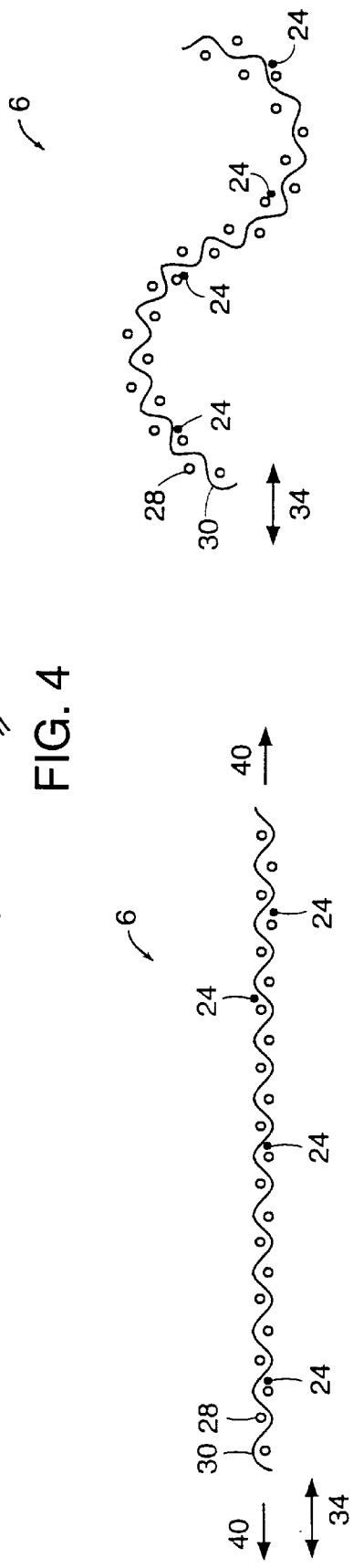

TOUCH FASTENER TAPE

BACKGROUND OF THE INVENTION

This invention relates to touch fastener tapes, such as for hook-and-loop fastening. Textile based touch fasteners are often used in the weft, or cross machine, direction. It is desirable for touch fasteners to exhibit elasticity in the weft direction for making secure closures.

SUMMARY OF THE INVENTION

The invention features a textile fastener tape characterized by having, in the weft direction across the tape, one or more sections which are elastically stretchable and one or more sections which are not stretchable. The fastener tape is produced on standard weaving machines, using warp and weft yarns in which selected warp yarns are elastic and are provided in patterns in which sections of the yarns have a component of its extent in the cross machine or weft direction. Alternatively, the fastener tape is produced on knitting machines using elastic warp yarns.

In a general aspect of the invention, the fastener tape includes a textile backing defining a warp and a weft direction and, in the weft direction, having a first region and second region. The first region is substantially non-stretchable in the weft direction and the second region is substantially elastically stretchable in the weft direction. An array of fastener elements extends from the first region.

A region of a fastener tape that is substantially elastically stretchable observably increases in length in response to a typical force applied to a fastener tape and, upon removal of the force, retracts to approximately the original length of the region.

A region of a fastener tape that is substantially non-stretchable does not observably increase in length in response to typical forces applied to a fastener tape.

Embodiments of this aspect of the invention may include one or more of the following features.

The fastener tape includes a third region having no fastener elements and which is substantially non-stretchable in the weft direction.

The second region of the fastener tape includes a warp pattern defined by inelastic warp yarns and elastic warp yarns having a portion extending in a weft direction for crossing at least one inelastic warp yarn. Many of the elastic warp yarns each cross more than one inelastic warp yarn. The textile backing is woven. The textile backing is a leno weave.

The textile backing is a knit.

The fastener tape is in the form of a fastener tab having a portion secured to an object and a portion protruding beyond the object having the first region with the fastener elements spaced from the object by the second region. The object is a garment (e.g. a diaper).

Other features and advantages will be apparent from the following description and claims.

BRIEF DESCRIPTION OF THE DRAWINGS

FIG. 1 is a plan view of a fastener tape.

FIG. 2 is a schematic illustration of a fabric from which the fastener tape is cut.

FIG. 3 is a side view of the fastener tape of FIG. 1.

FIG. 4 illustrates the structure of an elastic section of a woven fastener tape.

FIGS. 5A and 5B show the elastic section structure of a woven fastener tape under tension and relaxed, respectively.

DESCRIPTION

Figure 6:
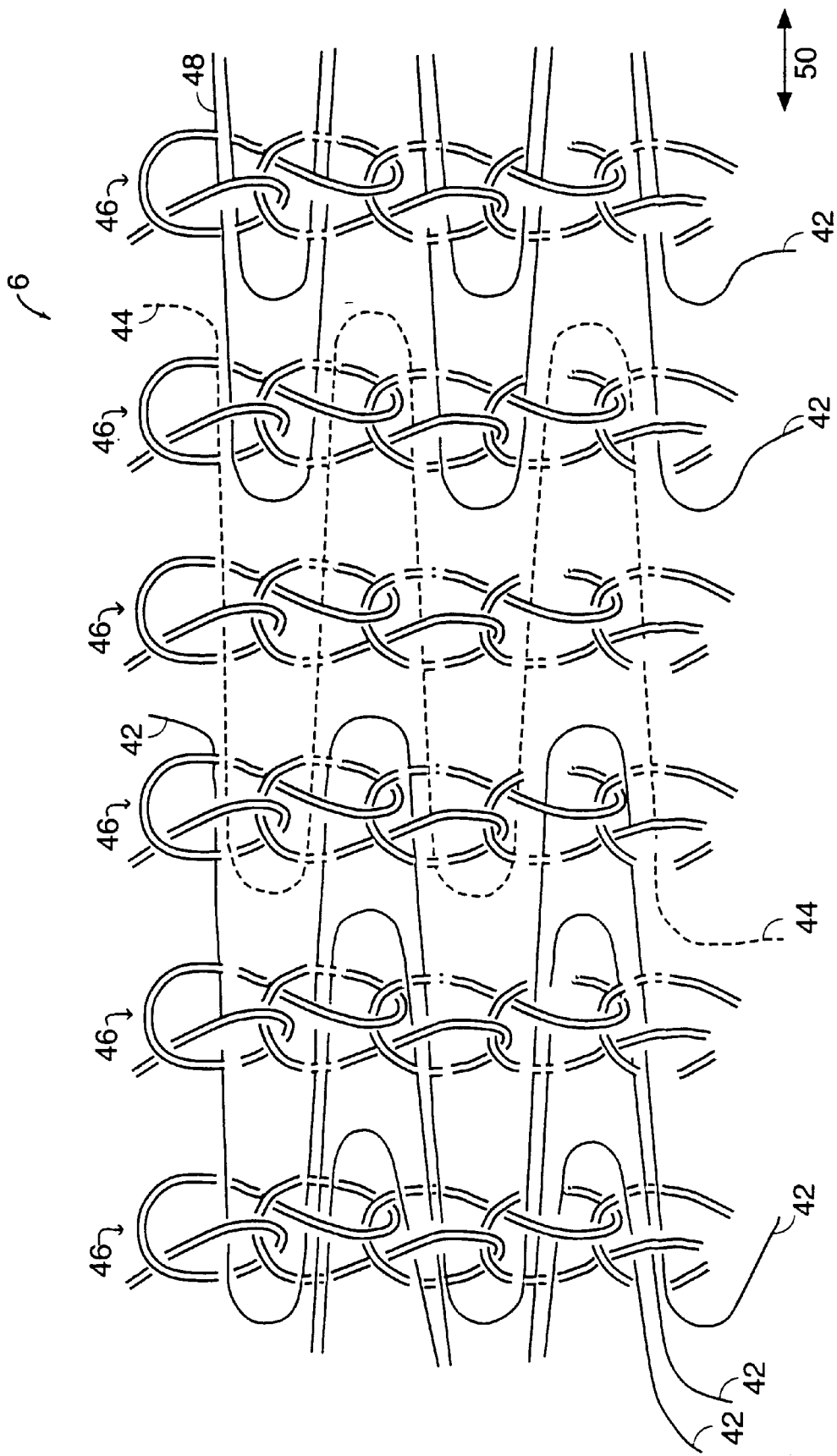
FIG. 6 illustrates the structure of an elastic section of a knit.

Referring to FIG. 1, a textile fastener tape 2 includes a fastener section 4, an elastic section 6, and a tab section 8 arranged sequentially across a length 10 extending in weft direction 12. Sections 4, 6, 8 exhibit different elastic behavior in weft direction 12. In response to a typical applied force along weft direction 12 of the fastener tape, fastener section 4 and tab section 8 do not substantially stretch while elastic section 6 does observably stretch.

Referring to FIG. 2, fastener tape 2 (FIG. 1) is produced from a fabric 14 which includes multiple fastener sections 4, elastic sections 6, and tab sections 8 that extend in warp direction 16. A portion of fabric 16 is cut as indicated by dotted line 18 to form the fastener tape 2 of FIG. 1.

Referring to FIG. 3, an array of male fastener elements 20 extends from a base fabric 22 of fastener tape 2 for the purpose of engaging cooperating fastener elements to make a closure. Male fastener elements 20 can be hook-shaped, as shown, or mushroom-shaped.

Referring to FIG. 4, elastic section 6 is manufactured by incorporating a number of elastic warp yarns 24 into a woven fabric 26 made primarily of inelastic warp yarns 28 and inelastic weft yarns 30. Elastic warp yarns 24 have weft direction components of extension. Localized sections 32 of warp yarns extend in weft direction 34 in addition to warp direction 36. As in a leno weave, elastic warp yarns 24 cross adjacent inelastic warp yarns 28. In some cases, individual elastic warp yarns 24 cross over multiple inelastic warp yarns 28.

Examples of elastic warp yarn 24 include elastomeric yarn (110 decitex), either single-component or coated, and lycra (235 decitex) coated with nylon. Elastic section 6 has a density of approximately seventeen elastic warp yarns 24 per one inch width fabric. In some cases, it is desirable to produce woven fabric 26 having multiple elastic sections 6 with different elastic properties (e.g. elongations).

Referring to FIG. 5A, a cross-section of a portion of elastic section 6 is placed under tension by a force, indicated by arrows 40, in weft direction 34. The force, for example, is applied during the weaving process used to manufacture fastener tape 2 and causes elastic warp yarns 24 to stretch in weft direction 34 while being incorporated into fabric 26 (FIG. 4). Alternatively, the force can be applied to fastener tape 2 in use. Elastic warp yarns 24 elongate in response to the force as elastic section 6 stretches.

Referring to FIG. 5B, when the force is removed elastic warp yarns 24 contract and elastic section 6 returns to an unstretched state. Woven fabric 26 forms a wave-like structure as inelastic warp yarns 32 crossed by elastic warp yarns 24 (FIG. 4) are pulled by the contraction.

Referring to FIG. 6, elastic section 6 of a knitted fabric 48 includes a series of wales 46, that is rows of loops that extend across knitted fabric 48, in between which elastic weft yarns 44 and inelastic weft yarns 42 are knitted. Elastic weft yarns 44 and inelastic weft yarns are knitted in between two non-adjacent wales 46 such that at least one wale 46 is common to both elastic weft yarn 44 and inelastic warp yarn 42. Because of extension in weft direction 50 of elastic weft yarns 44, elastic section 6 elastically stretches in response to a force applied to knitted fabric 48 in weft direction 50, as described with respect to woven fabric.

Other knitting patterns having different types of interlacing between elastic yarns 44 and inelastic yarns 42 may be employed to effect the elasticity of elastic section 6.

Figure 7:
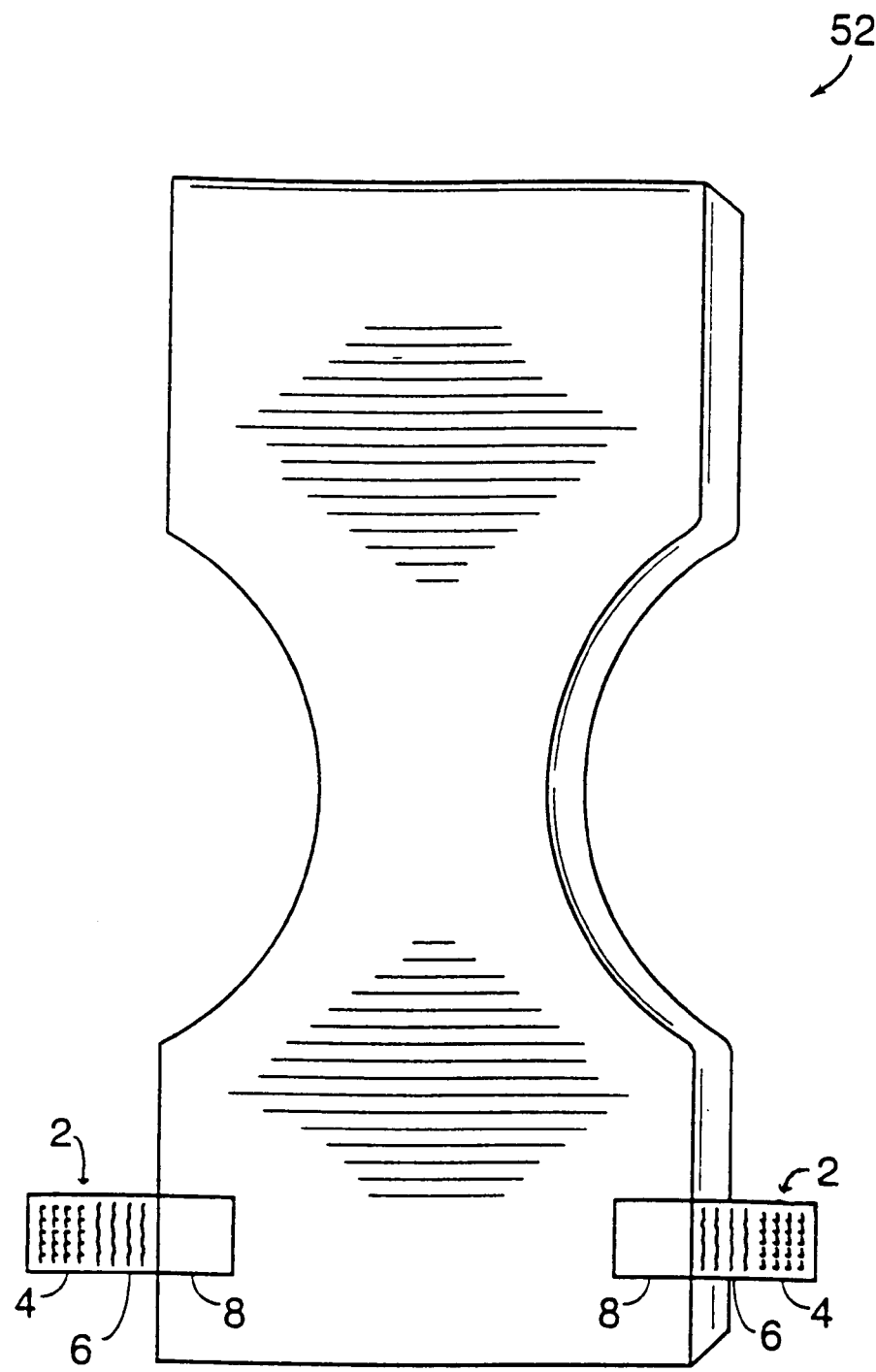
FIG. 7 shows the fastener tape on a diaper.

Referring to FIGS. 1 and 7, fastener tape 2 is used to secure a garment, in this case, diaper 52 around a human body. In use, fastener tape 2 is pulled in the weft direction to engage male fastener elements 20 (FIG. 3) of fastener section 4 with female fastener elements (not shown) on an opposite side of garment 52. As fastener tape 2 is pulled, elastic section 6 stretches in the weft direction while fastener section 4 and tab section 8 do not stretch. After fastener elements 14 are correspondingly engaged, the tendency for elastic section 6 to return to its unstretched state provides a force that secures diaper 52 around the body and helps to maintain the engagement of the closure.

Other features and embodiments are also within the scope of the following claims.

What is claimed is:

1. A fastener tape for attachment to an article comprising:

a textile backing formed by a predetermined pattern of selected yarns defining a warp direction and a weft direction, the textile backing, as a result of the predetermined pattern of selected yarns, having, in the weft direction, a first region that is substantially non-stretchable in the weft direction and a second region that is substantially elastically stretchable in the weft direction; and an array of fastener elements extending from the first region.

2. The fastener tape of claim 1 wherein the textile backing includes a third region having no fastener elements and which is substantially non-stretchable in the weft direction.

3. The fastener tape of claim 1 wherein the second region includes a warp pattern defined by inelastic warp yarns and elastic warp yarns, the elastic warp yarns each having a portion extending in a weft direction for crossing at least one of the inelastic warp yarns.

4. The fastener tape of claim 3 wherein the textile backing is woven and comprises a leno weave.

5. The fastener tape of claim 3 wherein many of the elastic warp yarns each cross more than one inelastic warp yarn.

6. The fastener tape of claim 1 wherein the textile backing comprises a knit.

7. The fastener tape of claim 1 in the form of a fastener tab having a portion secured to an object and a portion protruding beyond the object, the protruding portion having said first region with said fastener elements spaced from said object by said second region.

8. The fastener tape of claim 7 wherein the object comprises a garment.

9. The fastener tape of claim 8 wherein the garment comprises a diaper.

* * * * *